United States Patent
Wattler et al.

(10) Patent No.: US 6,924,146 B1
(45) Date of Patent: Aug. 2, 2005

(54) METHOD OF CONSTRUCTING VECTORS FOR HOMOLOGOUS RECOMBINATION DIRECTED MUTAGENESIS

(76) Inventors: Sigrid Wattler, 333 Holly Creek Court, The Woodlands, TX (US) 77381; Michael Nehls, 178 S. Cochrans Green Cir., The Woodlands, TX (US) 77381

( * ) Notice: Subject to any disclaimer, the term of this patent is extended or adjusted under 35 U.S.C. 154(b) by 0 days.

(21) Appl. No.: 09/171,642

(22) PCT Filed: Feb. 20, 1998

(86) PCT No.: PCT/US98/03243
§ 371 (c)(1),
(2), (4) Date: Oct. 21, 1998

(87) PCT Pub. No.: WO98/37175
PCT Pub. Date: Aug. 27, 1998

(30) Foreign Application Priority Data
Feb. 21, 1997 (DE) .......................... 197 07 012

(51) Int. Cl.$^7$ .................. C12N 15/74; C12N 15/63; C07H 21/02; C08B 11/193
(52) U.S. Cl. .................... 435/471; 435/455; 536/23.1; 536/91.4
(58) Field of Search ................ 800/8, 21; 536/23.1, 536/24.2, 91.4; 435/320.1, 91.1, 91.4, 440, 455, 471

(56) References Cited

U.S. PATENT DOCUMENTS

| | | | |
|---|---|---|---|
| 5,487,992 A | * 1/1996 | Capecchi et al. | ......... 435/172.3 |
| 5,589,369 A | * 12/1996 | Seidman et al. | ......... 435/172.3 |
| 5,650,550 A | * 7/1997 | Korach et al. | ................. 800/2 |
| 6,090,554 A | 7/2000 | Woychik | ....................... 435/6 |
| 6,090,629 A | 7/2000 | Woychik | .................... 435/472 |
| 6,528,313 B1 | 3/2003 | Le Mouellic | ............... 435/461 |
| 6,528,314 B1 | 3/2003 | Le Mouellic | ............... 435/461 |
| 6,537,542 B1 | 3/2003 | Treco | ..................... 424/93.21 |

OTHER PUBLICATIONS

Thorsten Storck, et al. *Rapid Construction in Yeast of Complex Targeting Vectors for Gene Manipulation in the Mouse.* Nucleic Acids Research, vol. 24, No. 22, pp. 4594–4596 (1996).
Krisher, RL et al. Journal of Diary Science 78(6):1282–1288, Jun. 1995.*
Nehls, m et al. Biotechniques 17(4):770–775, Oct. 1994.*
Storck, T. et al. Nucleic Acid Research 24(22):4594–4595, Nov. 1994.*
Seamark, R.F. Reproduction Fertility and Development 6:653–657, Jun. 1995.*

* cited by examiner

*Primary Examiner*—Joseph Woitach
(74) *Attorney, Agent, or Firm*—Benjamin Aaron Adler

(57) ABSTRACT

The present invention provides a novel vector system and thereby a novel method for the simplified construction of recombinant vectors for directed mutagenesis. Said vector system is used to modify the eukaryotic genome, particularly of embryonic stem cells, at precise and predefined loci by the means of homologous recombination. Furthermore, said system finds its usage in the generation of new strategies for gene therapy and in the generation of genetically modified higher eukaryotic organisms.

6 Claims, 4 Drawing Sheets

US 6,924,146 B1

METHOD OF CONSTRUCTING VECTORS FOR HOMOLOGOUS RECOMBINATION DIRECTED MUTAGENESIS

BACKGROUND OF THE INVENTION

1. Field of the Invention

The present invention relates to methods and vectors for making specific mutations in genes. More specifically, the invention relates to the use of a vector system useful in modifying the eukaryotic genome, particularly of embryonic stem cells, at precise and predefined loci by the means of homologous recombination.

2. Description of the Related Art

Many different technologies have been described that lead to chromosomal alterations and thereby to a modification of the structure and/or expression of genes. One technique for targeted mutagenesis is based on homologous recombination. The general methodologies of targeting mutations into the genome of cells, and the process of generating mouse lines from genetically altered embryonic stem (ES) cells with specific genetic lesions are well known (Bradley, 1991,*Cur. Opin. Biotech.* 2: 823–829).

A synthetic recombination vector which contains the genetic information of the targeted chromosomal locus recombines with the genomic DNA after introduction into a cell. The vector usually contains a positive selection cassette which is flanked by the genetic information of the target locus to enrich for cells where the vector successfully recombines with the chromosomal DNA against the pool of non-recombinant cells. Stable integration leads to a long term resistance against certain pharmacological toxins. Examples are the resistance against G418, i.e., Geniticin, or Hygromycin by the action of the neomycin or hygromycin resistance genes, respectively. The position of the positive selection cassette in the chromosomal vector DNA can further lead to a mutation of the gene as in classical knockout experiments, i.e., inactivation of gene function. Furthermore, inactivation or modification of regulatory elements of the target gene as well as of domains of the transcribed/translated gene product could have positive, negative or modulatory effects on future target gene function.

Homologous recombination, that is carried out by the target DNA flanking the positive selection cassette, has to be selected against the background of unwanted non-homologous recombination that is thought to occur over the vector ends. A negative selection cassette positioned at the terminus of the vector will frequently be integrated by the non-homologous recombination events. Stable expression of the negative selection marker leads to cytotoxicity of otherwise non-cytotoxic agents. An example is the activated cytotoxicity of Gancyclovir by the action of the Herpes Simplex virus thymidine kinase gene product (HSV-TK). The likelihood of obtaining a homologous recombination event increases with the size of the chromosomal vector DNA and is further dependent on the isogenicity between the genomic DNA of the vector and the target cell.

The cloning of large chromosomal fragments (5,000–15,000 base pairs) of the target gene, the subcloning of this DNA into a bacterial plasmid vector, the mapping of the gene structure, the integration of the positive selection cassette into the vector and finally, the flanking of one or both homologous vector arms by a negative selection marker is a technically demanding task and generally requires long construction times (3–6 months). The construction of the recombination vector itself is, therefore, most often the time limiting step in targeted mutagenesis experiments.

The prior art is deficient in the lack of effective means of constructing vectors for homologous recombination directed mutagenesis. The present invention fulfills this longstanding need and desire in the art.

SUMMARY OF THE INVENTION

An object of the present invention is to simplify the construction of vectors for the targeted mutation of genes by homologous recombination in mammalian cells. These vectors facilitate the construction of specifically mutated cells, cell lines derived from the individually mutated cells, and cells for the use in the production of transgenic non-human animals.

Another object of the present invention is to provide a vector system that avoids the drawbacks of conventional vector construction.

The present invention provide a vector system and a new procedure that simplifies the construction of positive/negative selection cassettes. This new method reduces the time required for the construction of such vectors from 3–6 months to about 14 days.

A particularly useful vector class contemplated by the present invention includes a linear lambda vector (lambdaKOS, i.e., knockout shuttle) for the construction of genomic DNA libraries that comprises: a stuffer fragment; an *E.coli* origin of replication; an antibiotic resistance gene; a yeast origin of replication; a selectable marker suitable for use in yeast; a negative selectable marker suitable for use in mammalian cells; LoxP sequences for Cre recombinase directed conversion of said linear lambda phage vector into an *E.coli*/yeast shuttle plasmid.

An additional vector contemplated by the present invention is a vector designed to specifically insert a positive selection cassette into cloned genomic DNA. The vector comprises an *E.coli* origin of replication; an antibiotic resistance gene; a selectable marker suitable for use in yeast; a positive selectable marker suitable for use in mammalian cells; unique restriction endonuclease sequences flanking the positive selectable marker so that the marker can be exchanged for another positive selection marker; unique restriction endonuclease sequences for the excision of the positive selection cassette of the vector and restriction endonuclease sequences flanking the bacterial and yeast sequences to facilitate the removal of these sequences from the vector after yeast-mediated recombination into the genomic target site of the shuttle plasmid.

An additional embodiment of the invention provides a method of generating mutations at specific sites in cloned genomic DNA, comprising the steps of: cloning genomic DNA into a linear lambda vector; isolating a clone of interest; converting the linear lambda vector containing the genomic DNA of interest into a circular *E.coli*/yeast shuttle vector; identifying genomic DNA sequences intended for targeting of the positive selection cassette; synthesizing deoxyoligonucleotides complementary to sequences flanking the site intended for targeting of the positive selection cassette to the circular genomic shuttle vector; attaching the deoxyolignucleotides to the positive selection cassette by ligation or PCR; co-transforming the *E.coli*/yeast shuttle vector containing the genomic DNA of interest and the modified positive selection cassette into a yeast host cell, wherein an intact recombinant plasmid is selected for by culturing the yeast on an appropriate media by means of the gene products provided for by two independent yeast selectable markers of the *E.coli*/yeast shuttle vector and the positive selection cassette and is obtained by performing homologous DNA recombination between homologous regions of the vector containing genomic DNA and the synthetically derived sequences which had been ligated onto the ends of the positive selection cassette thereby generating a new recombinant vector with the positive selection cassette inserted into the genomic DNA sequences. After yeast plasmid isolation, *E.coli* transformation and *E.coli* plasmid isolation, the *E.coli*/yeast sequences of the positive selection cassette vector are removed, comprising the steps of: digesting the new recombinant vector with restriction endonuclease specific for the unique restriction endonuclease sequences incorporated into the positive selection cassette vector which flank the *E.coli*/yeast sequences in the vector; ligating said digested vector; and identifying ligation products lacking the *E.coli*/yeast sequences desired to be removed.

Also provided is a method for the production of mutated animal cells consisting of: linearization of a new recombinant vector at a unique restriction endonuclease sequence outside the sequences of the cloned genomic DNA; introduction of linearized DNA into an animal cell; and selection of transduced cells that express a positive selectable marker. Preferably, the animal cells are embryonic stem cells or any other cell type with the potential to generate an animal.

In yet another embodiment of the present invention, there is provided a method for the production of non-human transgenic animal consisting of: introduction of mutated animal cells into animal embryos; placement of embryos containing mutated cells into the uterus of a female animal; and replacement of the nucleus of a fertilized egg with the nucleus containing the modified genomic DNA.

Further provided are genomic and sub-genomic libraries constructed in the linear lambda vector wherein the libraries are derived from genomic DNA isolated from the group consisting of animal cells, mammalian cells, rodent cells, murine cells and other higher eukaryotic cells.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

Figure 1:
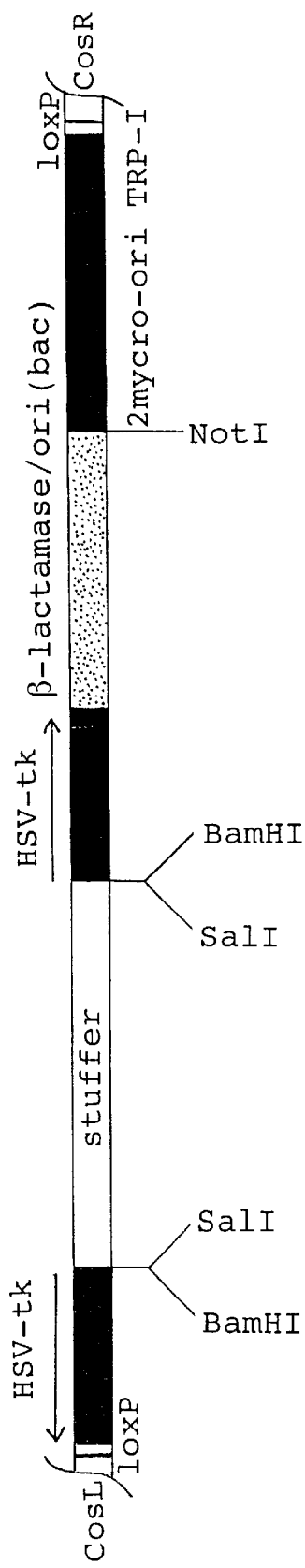
FIG. 1 shows a diagrammatic representation of a linear lambda vector (lambdaKOS) that is generally representative of the type of vector that may be used in the present invention.

As used herein, "insertional mutagenesis system" shall refer to a genetic system which allows one to mutate a genomic locus by inserting a genetic marker with or without replacing genomic sequences at the site of insertion.

As used herein, "targeted mutagenesis" shall refer to mutation of a genetic locus by inserting or replacing parts of the locus with a selection cassette. The site of mutation is generally selected by homologous recombination.

As used herein, "linear lambda vector" shall refer to DNA prepared from lambda phages which is linear as compared to DNA prepared from Cre-expressing bacteria which are infected with the lambda phage where the linear phage DNA is connected to circular plasmid DNA.

As used herein, "*E.coli*/yeast shuttle vector" shall refer to any plasmid which contains replication origins for plasmid survival, i.e., multiplication and selection in *E.coli* and yeast cells.

As used herein, "Cre recombinase" shall refer to the activity of the Cre recombinase protein, which recombines between short stretches of DNA comprising two LoxP elements.

As used herein, "lambdaKOS genomic library" shall refer to a collection of lambda phages which represent, by cumulative content of genomic DNA, either a total mammalian genome or a specified fraction thereof.

As used herein, "negative selection vector" shall refer to a vector containing a gene active in mammalian cells which allows the killing of such cells carrying the vector.

As used herein, "Cre/LoxP recombination system" shall refer to a system where the expression and activity of Cre-recombinase protein leads to a recombination effort between two cognate LoxP sequences.

The present invention describes a method of DNA vector construction to substantially improve the engineering of targeted mutation of genes by homologous recombination in mammalian cells. In one embodiment, the present invention provides an insertional mutagenesis system useful in constructing vectors for the targeted replication mutagenesis of mammalian cells by homologous recombination in which the mutagenesis system comprises: (a) a linear lambda vector for the cloning of genomic DNA to be flanked by negative selection markers; and (b) a vector for the insertion of a positive selection cassette into cloned genomic DNA.

The particularly unique features of this methodology include the construction of genomic DNA libraries in vectors with negatively selectable markers flanking the cloning sites and replication origins for *E.coli* and yeast cells to insert a positive selection cassette into the cloned genomic DNA sequences by homologous recombination in yeast directed by synthetic DNA sequences ligated onto the ends of a yeast replication deficient positive selection cassette and identical to the targeted genomic DNA sequences. This methodology simplifies the construction of positive/negative selection cassettes and furthermore reduces the time required for the construction of such vectors from 3–6 months to about 14 days.

A linear lambda vector (lambdaKOS) system was invented herein based on lambda phage cloning which allows the construction of representative genomic libraries of essentially every eukaryotic genome. This vector of the present invention comprises a stuffer fragment of DNA flanked by restriction endonuclease sequences to facilitate the replacement with and thereby the cloning of genomic DNA; an *E.coli* origin of replication; an antibiotic resistance gene; a yeast origin of replication; a selectable marker suitable for use in yeast; negative selectable markers suitable for use in mammalian cells; a direct repeat of recombinase sequences for recombinase directed conversion of the linear lambda phage vector into an *E. coli*/yeast shuttle plasmid. Preferably, this vector or any variants thereof are created by the use of different negative selectable markers. In this insertional mutagenesis system, the recombinase sequence and corresponding recombinase are selected from the group consisting of LoxP sequences-Cre recombinase and Frt sequences-Flp recombinase or any similar substitute as would be readily known to one having ordinary skill in this art.

An additional vector, i.e., the positive selection cassette vector, contemplated by the present invention is a vector designed to specifically insert a positive selection cassette into, cloned genomic DNA. This vector comprises a plasmid origin of replication; an antibiotic resistance gene; a selectable marker suitable for use in yeast; a positive selectable marker suitable for use in mammalian cells; unique restriction endonuclease sequences flanking the positive selectable marker so that the marker can be exchanged for another positive selection marker; a unique restriction endonuclease sequence for the linearization of the vector and restriction endonuclease sequences flanking the bacterial and yeast sequences to facilitate the removal of these sequences from the vector. Preferably, the positive selection cassette vector or any variants thereof are created by the use of a different positive selection marker.

An additional embodiment of the invention provides a method of generating mutations at specific sites in cloned genomic DNA, comprising the steps of: cloning genomic DNA into the linear lambda vector; isolating a clone of interest; converting the linear lambda vector containing the genomic DNA of interest into a circular *E.coli*/yeast shuttle vector by infecting a Cre reconibinase expressing bacterial strain; identifying genomic DNA sequences intended for targeting of the positive selection cassette; synthesizing deoxyoligonucleotides complementary to sequences flanking the site intended for targeting of the positive selection cassette to the circular *E.coli*/yeast shuttle vector; attaching the synthetic deoxyoligonucleotides to the positive selection cassette by ligation or PCR (see Example 2); co-transforming said *E.coli*/yeast shuttle vector containing the genomic DNA of interest and the modified positive selection cassette into a yeast host cell, wherein an intact recombinant plasmid is selected for by culturing yeast on an appropriate media by means of the gene products provided for by the yeast selectable markers of the *E.coli*/yeast shuttle vector and the positive selection cassette and is obtained by performing homologous DNA recombination between homologous regions of the vector containing genomic DNA and the synthetically derived sequences which had been ligated onto the ends of the positive selection cassette thereby generating a new recombinant vector with the positive selection cassette inserted into the genomic DNA sequences. Preferably, the *E.coli*/yeast sequences of the positive selection cassette vector are removed, comprising the steps of: digesting the new recombinant vector with restriction endonuclease specific for the unique restriction endonuclease sequences incorporated into the positive selection cassette vector which flank the *E.coli*/yeast sequences in the vector; ligating the digested vector; and identifying ligation products lacking the *E.coli*/yeast sequences desired to be removed.

The present invention is also directed to a method for the production of mutated animal cells consisting of: linearizing the recombinant vector at a unique restriction endonuclease sequence outside the sequences of the cloned genomic DNA; introduction of the linearized DNA into an animal cell; and selection of transduced cells that express the positive selectable marker. Preferably, the animal cells are embryonic stem cells.

The present invention is also directed to a method for the production of non-human transgenic animal consisting of: introduction of the mutated animal cells into animal embryos; placement of the embryos containing the mutated cells into the uterus of a female animal; and replacement of the nucleus of a fertilized egg with the nucleus containing the modified genomic DNA.

The present invention is further directed to genomic and sub-genomic libraries constructed in the linear lambda vector wherein said libraries are derived from genomic DNA isolated from the group consisting of animal cells, mammalian cells, rodent cells, murine cells and other higher eukaryotic cells.

The invention when compared to other techniques of homologous recombination vector construction offers the following advantages: First, the recombinant phage library has to be prepared only once for the particular genome of interest and can afterwards be amplified as a phage library in bacteria a million fold. Secondly, every gene locus is automatically ready for isolation with any gene probe of interest. Thirdly, the phage system allows the propagation of large chromosomal DNA which assists successful homologous recombination. Fourthly, a simple transfection of a Cre recombinase expressing bacterial strain creates a shuttle plasmid in which the genomic DNA is automatically flanked by negative selection cassettes. Fifthly, the shuttle plasmid not only allows the propagation in *E. coli* but also in yeast for which it can be selected for (TRP1) after successful transformation. Finally, the introduction of the positive selection cassette follows a published procedure (*Nucleic Acid Res.* 24:4594–4596) but is further improved by the herewith described and newly developed positive selection cassette and pMCS-1 which simplify the construction of variants.

In accordance with the present invention there may be employed conventional molecular biology, microbiology, immunology and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach,"Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription and Translation"[B. D. Hames & S. J. Higgins eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

The following terms shall have the definitions set out below. A "DNA molecule" refers to the polymeric form of deoxyribonucleotides (adenine, guanine, thymine, or cytosine) in either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure herein according to the normal convention of giving only the sequence in the 5' to 3' direction along the nontranscribed strand of DNA (i.e., the strand having a sequence homologous to the mRNA).

A DNA "coding sequence" is a double-stranded DNA sequence which is transcribed and translated into a polypeptide in vivo when placed under the control of appropriate regulatory sequences. The boundaries of the coding sequence are determined by a start codon at the 5'(amino) terminus and a translation stop codon at the 3'(carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

The term "oligonucleotide" or "deoxyoligonucleotide" as used herein is defined as a molecule comprised of two or more ribonucleotides or deoxyribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, the source of primer and the method used. For example, for diagnostic applications, depending on the complexity of the target sequence, the oligonucleotide primer typically contains 15–25 or more nucleotides, although it may contain fewer nucleotides.

As used herein, the term "PCR" refers to the polymerase chain reaction that is the subject of U.S. Pat. Nos. 4,683,195 and 4,683,202 to Mullis, as well as other improvements known in the art.

As used herein, the terms "restriction endonucleases" and "restriction enzymes" refer to bacterial enzymes, each of which cut double-stranded DNA at or near a specific nuclcotide sequence.

The labels most commonly employed for these studies are radioactive elements, enzymes, chemicals which fluoresce when exposed to ultraviolet light, and others. A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate.

The following examples are given for the purpose of illustrating various embodiments of the invention and are not meant to limit the present invention in any fashion.

EXAMPLE 1

Creation of Linear Lambda Vector (LambdaKOS)

A vector system was created based on lambda phage cloning which allows the construction of representative genomic libraries of essentially every eukaryotic genome. The linear lambda vector (lambdaKOS) has the following features from left to right (see FIG. 1): cos end and left arm of the phage, synthetic LoxP fragment, HSV-tk gene, endonuclease recognition sites BamHI and SalI, stuffer fragment, endonuclease recognition sites SalI and BamHI, HSV-tk gene, plasmid vector (bacterial origin of replication, β-lactamase gene for ampicillin resistance), endonuclease recognition sites NotI, yeast origin of replication 2micron, yeast auxotrophic TRP1 gene, synthetic LoxP fragment (same relative orientation as the previous one) and the right arm of the phage and cos end. DNA prepared from the lytic growing phage can be digested by the endonucleases SalI and BamHI and the stuffer fragment replaced by genomic DNA partially digested by the endonuclease Sau3AI. A several fold representative genomic library of a eukaryotic genome can thereby be established. Every genomic fragment (10,000–15,000 base pairs) is automatically flanked by a negative selection cassette on either site. Since the genomic library can be several fold redundant, virtually every genomic locus is represented by a lambdaKOS phage. Genomic clones of interest can be screened by classical filter hybridization of the lambda phage library. Infection of a Cre-recombinase expressing bacterial strain with a chosen phage clone leads to an automatic Cre mediated recombination of the lambda phage into a high copy *E.coli*/yeast shuttle plasmid (pKOS).

EXAMPLE 2

Insertion of Positive Selection Cassette (URA3/ CAT-Selection Cassette)

The insertion of the positive selection cassette (URA3/ CAT-selection cassette) into the genomic DNA of pKOS is carried out by cotransfection of the cassette with the particular pKOS plasmid into yeast and selection for complementation of both auxothrophic requirements of the TRP/ URA3-deficient yeast strain. The particular yeast strain used in this system requires the gene products of URA3 and TRP1 to survive and grow on selection plates. The TRP1 gene is delivered by the pKOS plasmid. The complementary URA3 gene is cotransfected as part of the replication deficient positive selection cassette.

Figure 3:
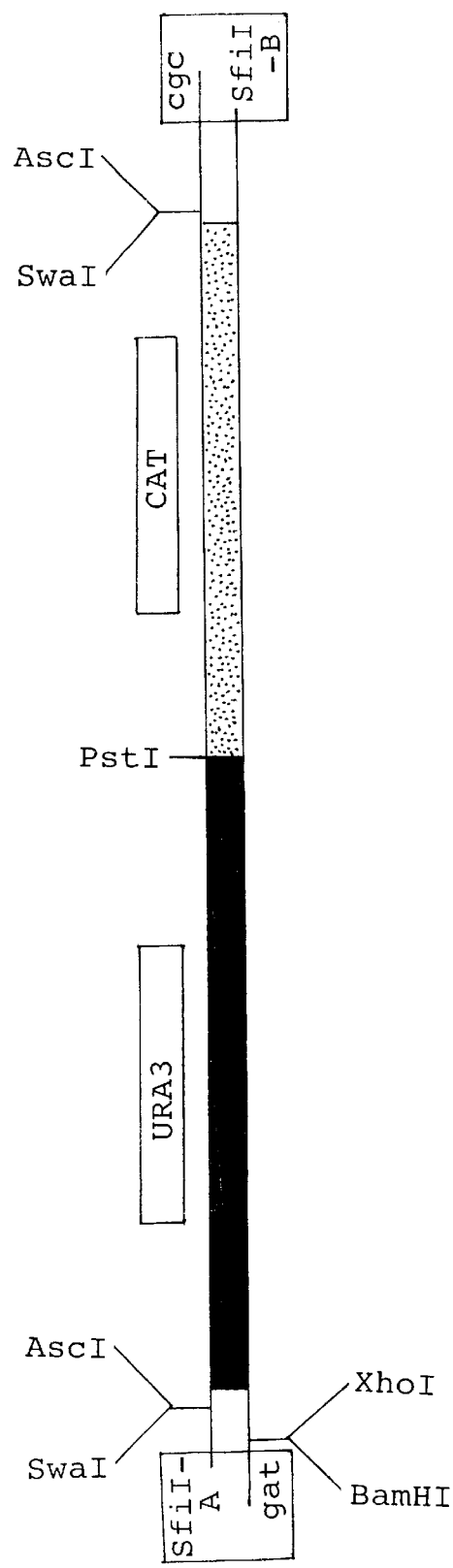
FIG. 3 shows an example of positive selection cassette. The complete URA/CAT-selection cassette can be removed by a digest with the endonuclease SfiI and replaced by any other desired positive selection cassette.

The URA3/CAT-selection cassette for cloning purposes is part of a high copy bacterial plasmid and has the following features (see FIG. 3): endonuclease recognition sites SfiI, BamHI, XhoI, SwaI and AscI, a yeast active URA3 gene, a bacterial active chloramphenicol acetyltransferase gene (CAT) gene and endonuclease recognition sites SwaI, AscI and SfiI. Any positive selection marker (e.g. neomycin or hygromycin expression cassettes) can be cloned into the endonuclease recognition sites BamHI and XhoI of the URA3/CAT-selection cassette prior to the yeast transfection.

Figure 2:
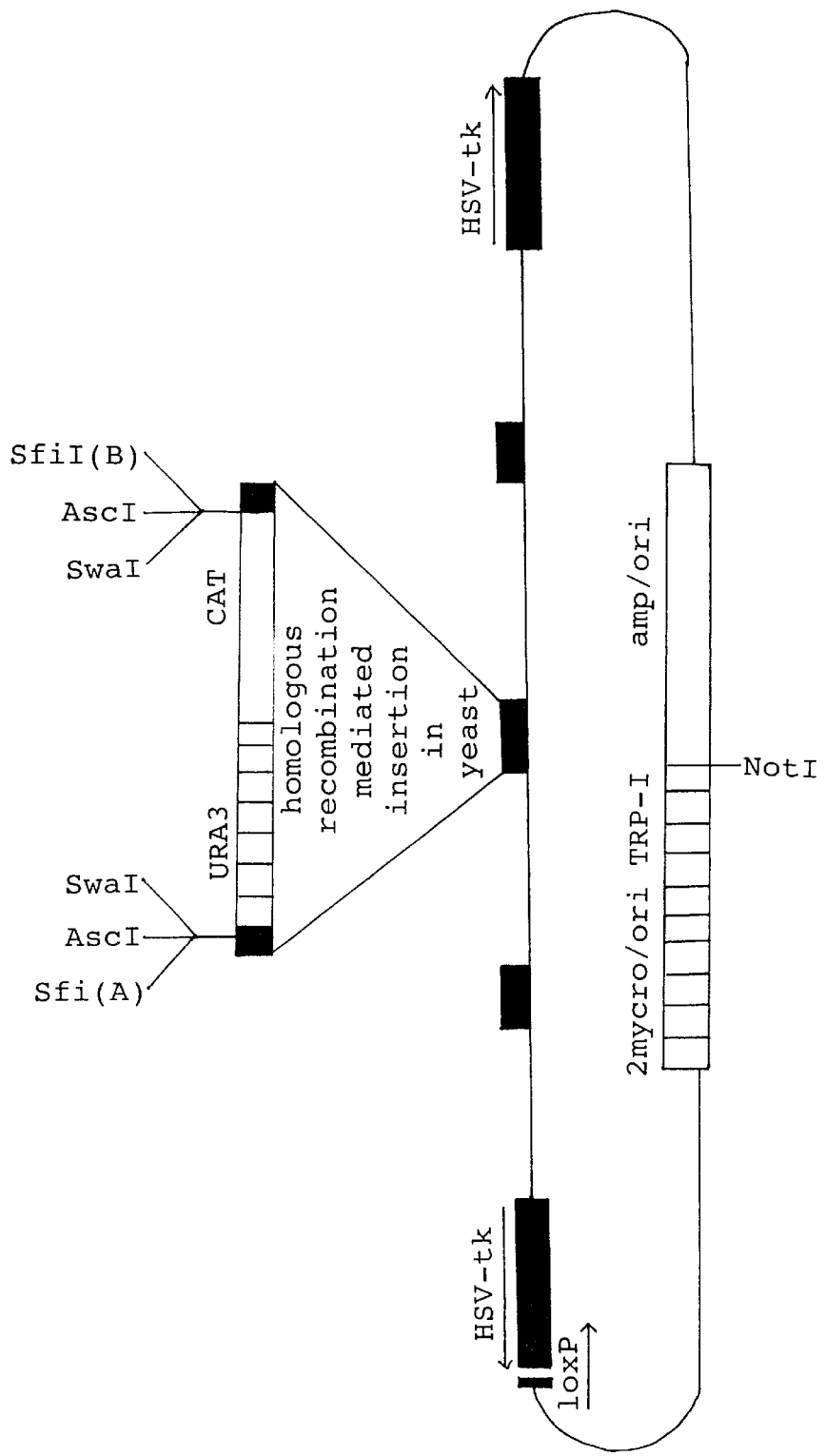
FIG. 2 shows a diagrammatic representation of a *E.coli*/yeast shuttle vector that is generally representative of the type of vector that may be used in the present invention, and shows a general strategy for the method of insertion of the positive cassette into the genomic DNA sequence.

Digestion of the URA3/CAT-selection cassette with the endonuclease SfiI will generate incompatible overhangs (see FIG. 2) to which synthetic double stranded oligonucleotides can be ligated. The sequences of the left and right oligonucleotides have to match the flanking sites of the desired integration site in the genomic DNA of the shuttle plasmid. Generally 40 base pairs of homology on both sites are sufficient for a successful integration of the positive selection cassette into the desired integration site of the pKOS plasmid. A very simple procedure to attach the 40 base pairs of homology is possible by the polymerase chain reaction (PCR) using oligonucleotide primers with the following features from 5' to 3': Primer A: 40 base pairs of homology with the 5' flanking sequence of the target locus and 15–20 base pairs of the 5' end of the positive selection cassette. Primer B: 40 base pairs of homology with the 3' flanking sequence of the target locus (opposite strand) and 15–20 base pairs of the 3' end of the positive selection cassette.

The generated URA3/CAT-selection cassette amplicon can be contransfected into the yeast strain with the pKOS plasmid of interest using standard procedures.

EXAMPLE 3

Further Selection for Homologous Recombinant Vectors

After successful cotransfection of the yeast replication incompetent positive selection cassette with the replication competent E.coli/yeast shuttle plasmid (pKOS), only the yeast cells survive on -URA/-TRP selection plates where the positive selection cassette recombines with the shuttle plasmid. The plasmids are recovered from the yeast cells and transferred into E.coli which allows a further selection by plating on chloramphenicol and ampicillin containing plates using standard procedures. Digestion of the plasmids with the endonuclease AscI or SwaI and re-ligation eliminates the URA3/CAT part of the completed pKOS recombination vector which can be selectively grown in bacteria in ampicillin containing media. Alternatively, the complete URA/CAT-selection cassette can be removed by a digest with the endonuclease SfiI and replaced by any other desired positive selection cassette.

Figure 4:
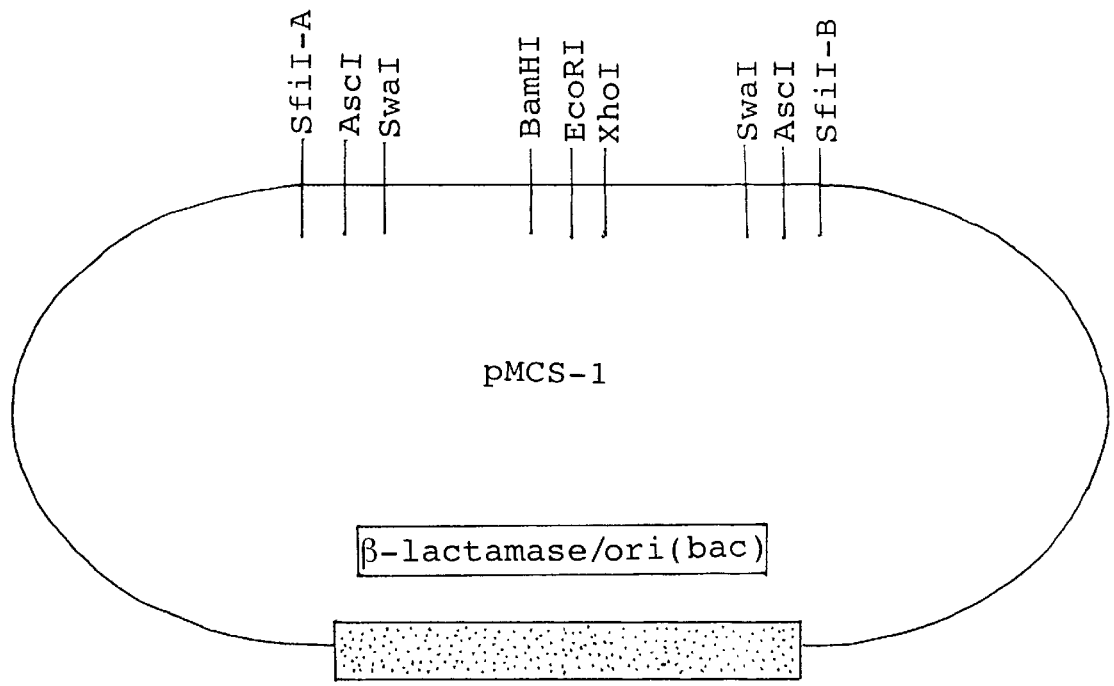
FIG. 4 shows pMCS-1 constructed as a new plasmid, comprising: an inverted repeat of three endonuclease restriction sites (SfiI, SwaI and AscI) flanking three unique endonuclease restriction sites (BamHI, EcoRI and XhoI) for the insertion of positive selection cassette. Any of the central three sites can be used to insert a selection cassette.

In order to improve this replacement procedure, a new plasmid was constructed, pMCS-1, which has the following features (see FIG. 4): an inverted repeat of three endonuclease restriction sites (SfiI, SwaI and AscI) flanking three unique endonuclease restriction sites (BamHI, EcoRI and XhoI) for the insertion of positive selection cassettes for later replacement of the URA3/CAT cassette from pKOS after yeast mediated recombination. Any of the central three sites can be used to insert a selection cassette, e.g., a neomycin, and any of the flanking sites can be used to swap the selection cassette with the pKOS inserted URA3/CAT cassette using the respective endonuclease restriction sites. Finally, for the gene targeting in mammalian cells via homologous recombination, the completed vector is linearized using the endonuclease NotI prior to transfection into the mammalian cells.

EXAMPLE 4

Generation of LambdaKOS Genomic Libraries

A lambdaKOS genomic library from the mouse inbred strain LEX-1 has been successfully generated with a 10 fold representation of the mouse genome and used successfully several times to recover pKOS clones of the desired genomic loci (6 of 6 independent trials) for homologous vector construction. In all cases the planned vector construction was carried out using the above discussed procedures and all insertions of the URA3/CAT-selection cassette were proceeded without any improper recombination events in yeast which would generate useless pKOS constructs. The proper recombination carried out by the yeast system leading to the integration of the positive selection cassette into the pKOS plasmid is, in itself, a surprise since pKOS carries two identical HSV-thymidine kinase (HSV-TK) cassettes which are a perfect substrate for a recombinant process. Since the two HSV-TK cassettes are constructed in pKOS with an inverted orientation, any recombination taking place between these two cassettes only leads to a inversion of intervening DNA but not to a deletion or other deleterious effects on the pKOS plasmid.

LambdaKOS genomic libraries or sublibraries are generally, but not exclusively, generated by cloning random fragments of genomic DNA between the phage arms. It is usually important to obtain sequence information from the inserted fragment ends in order to generate outside probes to analyze the mutated locus and to analyze and compare individual pKOS clones. Since the genomic insert is flanked on both sites by the HSV-TK cassettes, any pKOS sequencing primer oriented towards the insert would generate useless information. The construction of lambdaKOS allows the generation of two oligonucleotide primers which contain and reflect a single base pair different between the 5' end of the two HSV-TK cassettes:

KOS-1: 5'-accacactgctcgaggat

KOS-2: 5'-accacactgctcgacgga

Both primers allow a direct sequencing of both genomic insert ends, respectively.

EXAMPLE 5

The invented vector system consists of a completely new constructed lambda phage (lambdaKOS, i.e., knockout shuttle) which allows one to clone the complete genome of a eukaryotic organism in a negative selection vector to build a representative genomic library. This means every target gene of that genome is accessible for any planned mutation after one single cloning step (i.e., the generation of the genomic library) which has to be carried out only once for an individual eukaryotic cell. The phage, containing the desired genomic locus, can be isolated from the library which can easily be amplified and used for future clone isolation from other genomic loci. After an automatic subcloning step mediated by the Cre/LoxP recombination system, an E.coli/yeast shuttle plasmid (pKOS) can be obtained. The positive selection cassette is inserted into the plasmid by site-specific homologous recombination in yeast.

The invention as compared to other techniques of homologous recombination vector construction has the following advantages: the recombinant phage library has to be prepared only once for the particular genome of interest and can afterwards be amplified as a phage library in bacteria a million fold. Automatically, every gene locus is ready for isolation with any gene probe of interest. The phage system allows the propagation of large chromosomal DNA which assists successful homologous recombination. A simple transfection of a Cre recombinase expressing bacterial strain creates a shuttle plasmid in which the genomic DNA is automatically flanked by negative selection cassettes. The shuttle plasmid not only allows the propagation in E.coli but also in yeast for which it can be selected for (TRP1) after successful transformation. The introduction of the positive selection cassette follows a published procedure (*Nucleic Acid Res.* 24: 4594–4596) but is further improved by the herewith described newly developed positive selection cassette and pMCS-1 plasmid which simplify the construction of variants.

Any patents or publications mentioned in this specification are indicative of the levels of those skilled in the art to which the invention pertains. These patents an publications are herein incorporate by reference to the same extent as if each individual publication was specifically an individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, an specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

sequences which yield distinctive restriction fragment ends following SfiI digestion;

(6) distinct restriction endonuclease sites for the excision of the positive selective cassette prior to ligation of synthetic deoxynucleotides to the cassette ends; and (7) restriction endonuclease sequences flanking the bacterial and yeast sequences to facilitate the removal of these sequences from the vector.

What is claimed is:

1. An insertional mutagenesis system useful in constructing vectors for targeted mutagenesis of mammalian cells by homologous recombination, said insertional mutagenesis system comprising:

(a) a linear lambda vector for cloning of genomic DNA into a site flanked on each side by negative selection markers, wherein a negative selection marker is a gene which causes cytotoxicity when stably expressed and active in a cell; and (b) a vector for insertion of a positive selection cassette into cloned genomic DNA, wherein a positive selection cassette encodes a gene which when stably expressed confers resistance against certain pharmacological toxins, said vector comprising:

(1) an *E. coli* origin of replication;
(2) an antibiotic resistance gene;
(3) a selectable marker suitable for use in yeast;
(4) a positive selectable marker, wherein a promoter element is operatively positioned 5' to said positive selectable marker and a polyadenylation site operatively positioned 3' to said positive selectable marker;
(5) distinct SfiI restriction endonuclease sites flanking each side of the positive selectable marker so that said marker can be exchanged for another positive selection marker by directional cloning, wherein said SfiI sites are distinct in having different internal 2. The insertional mutagenesis system of claim 1, wherein said linear lambda vector comprising from left to right: cos end and left arm of the phage, a recombinase sequence, a first negative selectable marker, a stuffer fragment of DNA flanked by restriction endonuclease sequences to facilitate the cloning of genomic DNA, a second negative selectable marker with an inverted orientation relative to said first negative selectable marker, an antibiotic resistance gene, an *E.coli* origin of replication, a yeast origin of replication, a selectable marker suitable for use in yeast, a direct repeat of said recombinase sequence, and the right arm of the phage and cos end, wherein each of said negative selectable marker comprises a promoter element and a polyadenylation site operatively positioned 5' and 3' respectively to said negative selectable marker, and said recombinase sequences are for recombinase-directed conversion of the linear lambda phage vector into an *E. coli*/yeast shuttle plasmid.

3. The insertional mutagenesis system of claim 2, wherein said recombinase sequence and corresponding recombinase are selected from the group consisting of LoxP sequences-Cre recombinase and Frt sequences-Flp recombinase.

4. A method of generating mutations at specific sites in cloned genomic DNA, comprising the steps of:

(a) cloning genomic DNA into the linear lambda vector of claim 1;
(b) isolating a clone containing a genomic DNA of interest;
(c) generating a circular *E coli*/yeast shuttle vector by infecting a Cre recombinase expressing bacterial strain with said linear lambda vector containing the genomic DNA of interest;

(d) identifying an integration site in the genomic DNA sequences of said shuttle vector intended for targeting by the positive selection cassette of claim 1;

(e) synthesizing deoxyoligonucleotides complementary to sequences flanking said integration site;

(f) attaching said synthetic deoxyoligonucleotides to said positive selection cassette by ligation or PCR;

(g) co-transfecting said *E. coli*/yeast shuttle vector containing the genomic DNA of interest and said positive selection cassette with said synthetic deoxyoligonucleotides attached into a yeast host cell, wherein homologous DNA recombination between sequences flanking said integration site and said synthetic deoxyoligonucleotides ligated onto the ends of said positive selection cassette generates a new recombinant vector with the positive selection cassette inserted into the genomic DNA sequences, thereby generating mutations at specific sites in said genomic DNA.

5. The method of claim 4, further comprising the step of removing *E. coli*/yeast sequences from the positive selection cassette vector after said homologous DNA recombination.

6. The method of claim 5, wherein said removal comprises:

(a) digesting the recombinant t vector with the positive selection cassette inserted into the genomic DNA sequences with restriction endonuclease specific for distinct restriction endonuclease sites flanking the *E. coli*/yeast sequences in said positive selection cassette;

(b) ligating said digested vector; and (c) identifying ligation products lacking the *E.coli*/yeast sequences desired to be removed.

\* \* \* \* \*

SEQUENCE LISTING

```
<160> NUMBER OF SEQ ID NOS: 2

<210> SEQ ID NO 1
<211> LENGTH: 18
<212> TYPE: DNA
<213> ORGANISM: artificial sequence
<220> FEATURE:
<223> OTHER INFORMATION: Oligonucleotide primer from lambdaKOS which
      allows the direct sequencing of one of the genomic insert ends.

<400> SEQUENCE: 1
accacactgc tcgaggat                                                    18

<210> SEQ ID NO 2
<211> LENGTH: 18
<212> TYPE: DNA
<213> ORGANISM: artificial sequence
<220> FEATURE:
<223> OTHER INFORMATION: Oligonucleotide primer from lambdaKOS which
      allows the direct sequencing of the other genomic insert end.

<400> SEQUENCE: 2
accacactgc tcgacgga                                                    18
```